United States Patent
Tachon et al.

(10) Patent No.: US 11,766,387 B2
(45) Date of Patent: Sep. 26, 2023

(54) COSMETIC COMPOSITION SHOWING A NATURAL AND A HEALTHY-LOOKING APPEARANCE

(71) Applicant: L'OREAL, Paris (FR)

(72) Inventors: Romain Tachon, Kanagawa (JP); Sonia Eyraud, Chevilly la Rue (FR); Mathieu Chabrillangeas, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/608,530

(22) PCT Filed: Apr. 25, 2018

(86) PCT No.: PCT/EP2018/060628
§ 371 (c)(1),
(2) Date: Oct. 25, 2019

(87) PCT Pub. No.: WO2018/197576
PCT Pub. Date: Nov. 1, 2018

(65) Prior Publication Data
US 2020/0179242 A1     Jun. 11, 2020

(30) Foreign Application Priority Data
Apr. 26, 2017 (FR) ...................................... 1753650

(51) Int. Cl.
| | |
|---|---|
| *A61K 8/02* | (2006.01) |
| *A61K 8/04* | (2006.01) |
| *A61K 8/06* | (2006.01) |
| *A61K 8/29* | (2006.01) |
| *A61K 8/60* | (2006.01) |
| *A61K 8/64* | (2006.01) |
| *A61Q 1/02* | (2006.01) |

(52) U.S. Cl.
CPC ............ *A61K 8/0245* (2013.01); *A61K 8/042* (2013.01); *A61K 8/044* (2013.01); *A61K 8/062* (2013.01); *A61K 8/29* (2013.01); *A61K 8/60* (2013.01); *A61K 8/64* (2013.01); *A61Q 1/02* (2013.01); *A61K 2800/436* (2013.01); *A61K 2800/621* (2013.01); *A61K 2800/63* (2013.01)

(58) Field of Classification Search
CPC .......... A61K 8/19; A61K 8/042; A61K 8/044; A61K 8/062; A61K 8/29; A61K 8/60; A61K 8/64; A61K 8/0245; A61K 2800/63; A61K 2800/436; A61K 2800/621; A61Q 1/02
See application file for complete search history.

(56) References Cited

U.S. PATENT DOCUMENTS

| | | | |
|---|---|---|---|
| 4,744,832 A | 5/1988 | Franz et al. | |
| 2007/0134192 A1* | 6/2007 | Shimizu | ................... A61Q 1/10 424/70.31 |
| 2010/0028394 A1* | 2/2010 | Blin | ........................ A61K 8/375 424/401 |
| 2015/0150780 A1* | 6/2015 | Shimizu | ................... A61Q 1/04 424/401 |
| 2015/0157539 A1* | 6/2015 | Shimizu | ................... A61K 8/25 424/401 |
| 2015/0190320 A1* | 7/2015 | Tachon | ................ A61K 8/8152 424/401 |
| 2017/0042774 A1* | 2/2017 | Shimizu | ............... A61K 8/8129 |
| 2018/0071177 A1* | 3/2018 | Lee | ......................... A61K 8/19 |

FOREIGN PATENT DOCUMENTS

| | | |
|---|---|---|
| FR | 3 003 757 A1 | 10/2014 |
| JP | H08 259840 A | 10/1996 |
| JP | 2002 241231 A | 8/2002 |

OTHER PUBLICATIONS

Lourith et al. "Natural surfactants used in cosmetics: glycolipids" in International Journal of Cosmetic Science, 2009, 31, pp. 255-261. (Year: 2009).*

* cited by examiner

*Primary Examiner* — Blessing M Fubara
(74) *Attorney, Agent, or Firm* — POLSINELLI PC

(57) ABSTRACT

This invention relates to a cosmetic composition comprising, in a physiologically acceptable medium, at least one microcapsule comprising at least: —a core, —a first laminated coating surrounding said core comprising at least 45% by weight of the total weight, of a microcapsule of multilayer interference particles comprising at least one iron oxide, and —a second laminated coating surrounding said first coating, comprising between 10 and 40% by weight of titanium dioxide relative to the total weight of a microcapsule, said multilayer interference particles being released from said microcapsule(s) only when said composition is applied on a keratin material such as keratin fibers or the skin.

20 Claims, No Drawings

COSMETIC COMPOSITION SHOWING A NATURAL AND A HEALTHY-LOOKING APPEARANCE

CROSS REFERENCE TO RELATED APPLICATIONS

This application is a National Phase filing under 35 U.S.C. § 371 of PCT/EP2018/060628 filed on 25 Apr. 2018; which application in turn claims priority to Application No. 1753650 filed in France on 26 Apr. 2017. The entire contents of each application are hereby incorporated by reference.

This invention relates to a cosmetic composition designed for application on the skin, particularly for skin care, capable of providing a healthy-looking appearance for the skin while maintaining its natural appearance.

A composition according to the invention is intended particularly for application on the skin, and particularly facial skin.

Persons would frequently like to have a lighter, more homogeneous complexion when maintaining a non-shiny appearance.

It is known that skin can lose its radiance and become dull in the long term, particularly due to the effect of aging, and/or due to environmental factors such as pollution, wind or cold, for psychological reasons such as fatigue or stress, or due to hormonal changes such as the menopause. Similarly, some skins may have a dull complexion with a gray pallor.

Consequently, there is still a need for a cosmetic composition that can restore a skin tone with a brighter and more homogeneous appearance, in short conferring a healthy-looking appearance.

Classically, in order to obtain this healthy-looking appearance, makeup products are used containing coloring materials or pigments at individual concentrations of generally more than 1% by weight of the composition (foundation, "BB cream" type compositions) that are specific in that:
  they generate a strong covering effect, and
  they provoke a negative impact on the cosmetic properties of the basic composition, namely the composition considered without said coloring materials or pigments, precisely due to this content of coloring materials or pigments. A slowing effect in application, a lower perception of moisturization, a skin drying effect, and a feeling of dry or even rough skin are usually observed.

In other words, the use of classical compositions designed to improve the healthy-looking appearance actually result in an imperfect, poorly homogeneous colored effect, sometimes an almost unnatural metalized appearance that has the major disadvantage of concealing the natural appearance of the skin. Therefore after application, these compositions do not have a natural effect on the skin.

Therefore there is a need for cosmetic compositions that make the skin more radiant and introduce a healthy-looking appearance, while maintaining its natural appearance and attractive cosmetic properties particularly in terms of sensorial properties.

This invention satisfies these expectations.

Thus, according to one of its first aspects, the purpose of the invention is a cosmetic composition comprising, in a physiologically acceptable medium, at least one microcapsule comprising:
  a core,
  a first laminated coating surrounding said core comprising at least 45% by weight of the total weight, of a microcapsule, of multilayer interference particles comprising at least one iron oxide, and
  a second laminated coating surrounding said first coating, comprising between 10% and 40% by weight of titanium dioxide relative to the total weight of a microcapsule,
said multilayer interference particles being released from said microcapsule(s) only when said composition is applied on a keratin material such as keratin fibers or the skin.

Such a composition is intended particularly to confer a homogeneous healthy-looking appearance on the skin to which it is applied, and to provide a pinkish tone while preserving the natural appearance of the skin. If applicable, such a composition can also have the effect of dissimulating skin imperfections. Cosmetic properties similar to the properties of skin care compositions are obtained. In particular, the use of such a composition can provide improved cosmetic properties and more particularly sensorial properties for the consumer, related to slip during application and softness and comfort after use. Such a composition also has very limited covering power; consequently the skin keeps a natural appearance particularly because there are no additional skin coloring materials.

Furthermore, the composition according to this invention has the advantage that it guarantees a beneficial effect on the color resulting in an immediate healthy glow/brightness effect and maintenance of cosmetic properties, and more particularly sensorial properties resulting from slip during application, and user comfort after application.

This invention also has the advantage that all these properties are obtained immediately after the composition has been applied onto the skin.

A composition according to the invention is suitable for application onto skins with a dull tint, with little or no luster, and on which there can be blemishes and/or non-homogeneities.

Another purpose of this invention is a method of conferring a homogeneous healthy glow appearance and a pinkish tone on skin and particularly facial skin, while preserving the natural appearance of the skin, consisting of applying at least one layer of a composition conforming with the invention on the surface of the target skin, and particularly facial skin.

For the purposes of this invention, the terms "cosmetic property" and "cosmeticity" can be used indifferently.

The term "healthy-looking appearance" means obtaining a pinkish and radiant complexion.

The skin color can be defined for the purposes of this invention using the phototypes defined in Fitzpatrick's classification (see particularly Fitzpatrick, T. B., 1975, "Soleil et peau" [Sun and skin], Journal de Médecine Esthétique (2): 33-34; Pathak, M. A.; Jimbow, K.; Szabo, G.; Fitzpatrick, T. B. (1976). "Sunlight and melanin pigmentation". In Smith, K. C. (ed.): Photochemical and photobiological reviews, Plenum Press, New York, 1976: 211-239; Fitzpatrick, T. B. (1986). "Ultraviolet-induced pigmentary changes: Benefits and hazards", Therapeutic Photomedicine, Karger, vol. 15 of "Current Problems in Dermatology", 1986: 25-38)

Compositions according to the invention are particularly well adapted to phototypes I to V, and more preferably to phototypes I to III.

For the purposes of this invention, the term "keratinic material" is intended to include the skin, mucous membranes such as the lips, nails and eyelashes. This invention is particularly applicable to the skin and the lips, and particularly facial skin.

Microcapsules

Microcapsule(s) present in the composition according to the invention include at least:
- a core,
- a first laminated coating surrounding said core comprising at least 45% by weight of the total weight, of a microcapsule of multilayer interference particles comprising at least one iron oxide, and
- a second laminated coating surrounding said first coating, comprising between 10% and 40% by weight of the total weight of a titanium dioxide microcapsule.

The term "microcapsule" as used herein refers to a spherical microcapsule containing at least a first and a second laminated coating and surrounding a core chemically different from the first and the second coatings. Microcapsules are distinct from microspheres, that are composed of a homogeneous spherical matrix.

The microcapsules according to the invention are capable of permanently keeping multilayer interference particles in the microcapsule during storage of the composition, and thus efficiently prevent any undesirable modification to the stability of the composition, while keeping an unchanged visual effect of said composition in the long term. The composition according to the invention is visually homogeneous.

This invention also describes a method of preparing microcapsules. The method includes:
- preparation of an aqueous solution containing water and a first hydrophilic polymer,
- dispersion of multilayer interference particles comprising at least one iron oxide in the aqueous solution,
- formation of an internal layer (i.e. first laminated coating) on a core with the aqueous solution in which the multilayer interference particles are dispersed,
- the formation of an intermediate layer (i.e. second laminated coating) on the internal layer with a solution of titanium dioxide containing water and a second hydrophilic polymer, and
- preferably, the formation of an external layer on the intermediate layer with a solution containing water and a third hydrophilic polymer, on condition that the aqueous solution advantageously includes no hydrophobic solvent.

This invention also discloses the microcapsule obtained by this process.

The composition according to the invention preferably comprises between 0.1% and 20% by weight and preferably 0.3% and 15% by weight of microcapsules relative to the total weight of said composition, even better between 0.5% and 5%, and preferably between 0.7% and 3% by weight.

In particular, the multilayer interference particles are only present, i.e. encapsulated, in the first laminated coating of the microcapsules, and possibly in the second laminated coating.

The term "encapsulated" means that the multilayer interference particles are always trapped inside microcapsules according to the invention.

The microcapsules according to the invention may include an external layer. This external layer is always free of reflecting particles. Advantageously, the external layer is free of reflecting particles and preferably comprises at least one hydrophobic polymer and possibly a binder. Such a binder, in other words a hydrophilic polymer, can be chosen from among a hydrophilic polymer such as starch, cationic starch, cellulose, modified cellulose, mannitol, saccharose, polyvinyl alcohol and carrageenan.

Chemical Nature of Microcapsules

According to one preferred embodiment, the core is an organic core.

Advantageously, the core accounts for 1% to 50% by weight, preferably 5% to 30% by weight, and particularly 10% to 20% by weight with respect to the total weight of the microcapsule.

Advantageously, the size of the microcapsules varies from 10 μm to 500 μm, and particularly from 75 to 250 μm.

According to one preferred embodiment, the microcapsules comprise:
- a core comprising at least one organic material,
- at least one first laminated coating surrounding said core, the laminated coating comprising at least 45% by weight of the total weight of a microcapsule of multilayer interference particles comprising at least one iron oxide, and a binder chosen from among a hydrophilic polymer, a lipid based material, or mixtures thereof,
- a second laminated coating surrounding said first coating, comprising between 10% and 40% by weight of the total weight of a titanium dioxide microcapsule, and
- an outer layer comprising a hydrophilic polymer.

In one particular embodiment, the organic material of the core is chosen from among organic materials with good solubility in water. Preferably, the core is soluble in water or dispersible in water.

In one particular embodiment, the core is composed of a single compound, preferably an organic compound.

Preferably, the core comprises at least one monosaccharide or its derivatives as its organic material, and particularly a polyol monosaccharide advantageously chosen from among mannitol, erythritol, xylitol, sorbitol and mixtures thereof, and preferably mannitol.

Preferably, the core comprises at least one polyol monosaccharide, preferably chosen from among mannitol, erythritol, xylitol and sorbitol, and the first laminated coating surrounding said core and possibly the second laminated coating comprises at least one polysaccharide (or its derivatives) comprising at least one or several D-glucose units, preferably chosen from among starch and starch derivatives, celluloses and cellulose derivatives, preferably starch or starch derivatives.

In one particular embodiment, the core is composed of mannitol and more particularly exclusively mannitol.

According to one variant embodiment, the core contains at least mannitol and at least one hydrophilic polymer, particularly as described below. In particular, such a core may comprise mannitol and hydrophilic polymers chosen from among cellulose polymers, starch polymers and mixtures thereof. In one preferred embodiment, the cellulose polymer is a carboxymethylcellulose and the starch polymer is an unmodified natural starch, for example corn starch.

Preferably, the quantity of mannitol present is 2% to 100% by weight, preferably 5% to 100% by weight, and particularly 100% by weight with respect to the total weight of the core.

Preferably, the quantity of mannitol present is 1% to 50% by weight, preferably 4% to 40% by weight, and preferably 5% to 30% by weight, and particularly 10% to 20% by weight with respect to the total weight of the microcapsule.

Preferably, the first laminated coating surrounding said core, and possibly the second laminated coating, comprise at least one hydrophilic polymer.

Such a hydrophilic polymer is soluble or dispersible in water or in alcoholic compounds, chosen particularly among lower alcohols, glycols and polyols.

For the purposes of this patent application, the term "hydrophilic polymer" means a (co)polymer capable of forming one or more hydrogen bonds with water or alcoholic compounds, chosen particularly from among lower alcohols, glycols and polyols.

According to one particular embodiment of the invention, the hydrophilic polymer can inflate or soften in contact with water or alcoholic compounds, chosen particularly from among lower alcohols, glycols and polyols.

The hydrophilic compound can be chosen from among the following polymers:

- homopolymers or copolymers of acrylic or methacrylic acid or their copolymers or salts and esters, and particularly products marketed under the name Versicol F or Versicol K by Allied Colloid, Ultrahold 8 by Ciba-Geigy and Synthalen K type polyacrylic acids and their salts, and particularly sodium salts of polyacrylic acids, and more particularly a cross-linked sodium polyacrylate;
- acrylic and acrylamide acid copolymers sold in the form of sodium salts such as Reten by Hercules, sodium polymethacrylate marketed under the name Darvan No. 7 by Vanderbilt, and sodium salts of polyhydroxycarboxylic acids sold under the name Hydagen F by Henkel,
- copolymers of polyacrylic acid/alkyl acrylate, preferably modified or unmodified carboxyvinylic polymers. The copolymers used most preferably according to this invention are acrylate/C10-C30 alkyl acrylate copolymers (INCI name: acrylates/C10-30 alkyl acrylate crosspolymer) such as products sold by Lubrizol under the tradenames Pemulen TR1, Pemulen TR2, Carbopol 1382 and Carbopol ETD 2020, and even more preferably Pemulen TR-2;
- alkylacrylic acid/alkylmethacrylic copolymers and derivatives thereof, particularly their salts and their esters, such as ethyl acrylate copolymer, methyl methacrylate and the low content of methacrylic acid ester with quaternary ammonium groups supplied under the EUDRAGIT RSPO trade name by Evonik Degussa;
- AMPS (polyacrylamidomethylpropanesulfonic acid partially neutralized with ammonia and highly crosslinked) sold by Clariant;
- AMPS/acrylamide copolymers such as the Sepigel or Simulgel products sold by the SEPPIC company, particularly a copolymer with the INCI name Polyacrylamide (and) C13-14 Isoparaffin (and) Laureth-7;
- AMPS/polyoxyethylenated alkyl methacrylate (cross linked or not) copolymers such as Aristoflex HMS sold by Clariant;
- polysaccharides and derivatives, such as:
- anionic, cationic, amphoteric or non-ionic chitin or chitosan polymers;
- cellulose polymers and derivatives, preferably other than alkylcellulose, chosen from among hydroxyethylcellulose, hydroxypropylcellulose, hydroxypropylmethylcellulose, hydroxymethylcellulose, ethylhydroxyethylcellulose, carboxymethylcellulose, and quaternized cellulose derivatives; In one preferred embodiment, the cellulose polymer is a carboxymethylcellulose;
- polymers of starch and its derivatives, possibly modified. The starch that can be used with this invention usually originates from plant raw materials such as rice, soy, potatoes or maize. The starch can be unmodified starch or (by analogy with cellulose) modified starch. In one preferred embodiment, the starch is not modified (natural);
- polymers with natural origin, possibly modified, such as galactomannans and derivatives of them such as konjac gum, gellan gum, fenugrec gum, karaya gum, tragacanth, gum arabic, gum acacia, guar gum, hydroxypropylguar, hydroxypropylguar modified by sodium methylcarboxylate groups (Jaguar XC97-1, Rhodia), guar hydroxypropyltrimonium chloride and derivatives of xanthan;
- alginates and carrageenans;
- glycosaminoglycanes, hyaluronic acid and derivatives thereof;
- mucopolysaccharides such as hyaluronic acid and chondroitin sulfates, and mixtures thereof;
- vinyl polymers, for example polyvinylpyrrolidones, methylvinyl ether and malic anhydride copolymers, vinyl acetate and crotonic acid copolymer, vinylpyrrolidone and vinyl acetate copolymers; vinylpyrrolidone and caprolactam copolymers; polyvinyl alcohol;

and mixtures thereof.

Advantageously, the first laminated coating surrounding said core and possibly the second laminated coating comprises at least one or several hydrophilic polymers chosen from among polysaccharides and derivatives, homopolymers or copolymers or copolymers of acrylic or methacrylic acids or their salts and esters, and mixtures thereof. The polysaccharides and derivatives are preferably chosen from among chitosan polymers, chitin polymers, cellulose polymers, starch polymers, galactomannans, alginates, carrageenans, mucopolysaccharides and derivatives thereof and mixtures thereof, preferably starch polymers and derivatives thereof, cellulose polymers and derivatives thereof, and mixtures thereof.

In particular, the hydrophilic polymer is chosen from among polysaccharides and derivatives thereof, including one or several types of oses, preferably several types of oses including at least D-glucose units.

In particular, the hydrophilic polymer is chosen from among starch and derivatives thereof, celluloses and derivatives thereof, preferably starch and derivatives thereof.

Preferably, the microcapsule according to the invention has an outer layer. Advantageously, the external layer of the microcapsule is free of reflecting particles and preferably comprises at least one hydrophilic polymer and possibly a binder.

Preferably, the external layer comprises at least one hydrophilic polymer defined in the above list. Preferably, this hydrophilic polymer is chosen from among starch polymers and derivatives thereof.

Preferably, the microcapsules comprise at least one lipid-based material, preferably with amphiphilic properties such as lecithins and particularly hydrogenated lecithin.

According to one particular embodiment of this invention, such a lipid-based material can have amphiphilic properties, in other words an apolar part and a polar part.

Such a lipid-based material may comprise at least one or several C12-C22 fatty acid chains such as those chosen from among stearic acid, palmitic acid, oleic acid, linoleic acid, linolenic acid and mixtures thereof. Preferably, these fatty acid chains are hydrogenated. Finally, these fatty acid chains can be the apolar part of a lipid-based material.

Such a lipid-based material is preferably chosen from among phospholipids. It is preferably chosen from among phosphoacylglycerol, lecithins, and particularly hydrogenated lecithin.

The lipid-based material can represent 0.05 to 5% by weight of the microcapsule, and particularly 0.1 to 1% by weight of the microcapsule.

According to one particular embodiment of the invention, the microcapsules comprise at least:

a core comprising at least one monosaccharide-polyol, preferably mannitol, a first laminated coating surrounding said core comprising at least 45% by weight of the total weight of a microcapsule of multilayer interference particles comprising at least one iron oxide, and a hydrophilic polymer, a second laminated coating surrounding said first coating comprising 10% to 40% by weight of titanium dioxide relative to the total weight of a microcapsule, and a hydrophilic polymer and a lipid-based material, preferably hydrogenated lecithin.

Multilayer Interference Particles Comprising at Least One Iron Oxide

The multilayer interference particles present in the microcapsules and comprising at least one iron oxide are preferably nacres. These multilayer interference particles are present at least in the first coating of the microcapsules. The multilayer interference particles used in the present invention are also called reflecting particles.

"Nacre" denotes particles in the form of a multitude of thin platelets with a high refraction index, each of which partially reflects and transmits incident light, these particles also being called "interference pigments".

The cosmetic composition according to the invention may comprise between 0.1% and 5% by weight, preferably between 0.5% and 4% by weight and even better between 0.7% and 3% by weight of multilayer interference particles comprising at least one iron oxide, preferably nacres, relative to the total weight of said composition.

In one preferred embodiment, said nacre is chosen from among composite particles comprising at least one support chosen from among mica, synthetic fluorphlogopite or calcium sodium borosilicate and partially or completely coated with one or several iron oxide layers. Said nacre may include one or several other metal oxides, particularly chosen from among titanium dioxide, bismuth oxichloride, tin oxide and mixtures thereof.

The nacres can be chosen from among pearly pigments such as titanium mica coated with iron oxide, and pearly pigments based on bismuth oxichloride. They may also be mica particles at the surface whereof are superposed one or several successive layers of iron oxide and possibly other metal oxides and/or of organic dyes. They may also be and preferably are synthetic fluorphlogopite particles coated with iron oxide and possibly titanium dioxide, bismuth oxychloride and/or tin oxide.

Examples of nacres that could also be mentioned include natural mica coated with iron oxide and possibly titanium oxide, natural pigment and/or bismuth oxychloride.

Among the nacres available on the market, mention may be made of the Timica, Flamenco and Duochrome nacres (based on mica) sold by Engelhard, the Timiron nacres sold by Merck, Prestige Mica nacres sold by Eckart and nacres based on Sunshine synthetic mica sold by Sun Chemical.

The nacres may more particularly have a yellow, pink, red, bronze, orange, brown, gold and/or copper glint.

As an illustration of nacres that can be used in the context of this invention, mention may be made of the gold nacres sold specially by Engelhard under the name Brilliant Gold 212G (Timica), Golden Bronze (Timica), Gold 222C (Cloisonne), Sparkle gold (Timica), Gold 4504 (Chromalite) and Monarch gold 233X (Cloisonne); the bronze nacres sold specially by Merck under the name Bronze fine (17384) (Colorona) and Bronze (17353) (Colorona) and by Engelhard under the name Super bronze (Cloisonne); the orange nacres sold specially by Engelhard under the names Orange 363C (Cloisonne) and Orange MCR 101 (Cosmica) and by Merck under the names Passion orange (Colorona) and Matte orange (17449) (Microna); the brown-hued nacres sold specially by Engelhard under the names Nu-antique copper 340XB (Cloisonne) and Brown CL4509 (Chromalite); the copper-glint nacres sold specially by Engelhard under the name Copper 340A (Timica); the red-glint nacres sold specially by Merck under the name Sienna fine (17386) (Colorona); the yellow-glint nacres sold specially by Engelhard under the name Yellow (4502) (Chromalite); the gold-glint red-hued nacres sold specially by Engelhard under the name Sunstone G012 (Gemtone); the pink nacres sold specially by Engelhard under the name Tan opal G005 (Gemtone); the gold-glint black nacres sold specially by Engelhard under the name Nu-antique bronze 240 AB (Timica), the blue nacres sold specially by Merck under the name Matte blue (17433) (Microna), the silver-glint white nacres sold specially by Merck under the name Xirona Silver and the green-gold and pinkish orangish nacres sold specially by Merck under the name Indian summer (Xirona) and mixtures thereof.

Preferably, the nacres that can be used with this invention have a grade h between 0 and 90, and preferably between 30 and 60. This grade is evaluated by means of a KONICA MINOLTA CM700d colorimeter, after application of nacres on a white support with a concentration of 0.2 mg/cm$^2$. The color is characterized by the C.I.E. L*C*h* system in which the value h denotes the HUE, the value c is SATURATION, and the value L denotes the LIGHTNESS.

More precisely, the preferred nacres are as follows:

| Trade name | Mica | Synthetic fluorphlogopite | TiO2 CI77891 | Iron oxide CI77491 | Tin oxide | Carmin CI75470 | Bismuth oxichloride | L_white | C_white | h_white |
|---|---|---|---|---|---|---|---|---|---|---|
| Syncrystal Almond | | 67 | 12 | 20 | 1 | | | 73.8 | 30.3 | 45.3 |
| Timica Golden Bronze | 62 | | 3 | 35 | | | | 67.1 | 39 | 54.1 |
| Gemtone Tan Opal | 61.5 | | 14.5 | 24 | | | | 74.8 | 25.6 | 47.7 |
| Gemtone Garnet | 53 | | 43 | 3 | | 1 | | 84.1 | 14.7 | 39.9 |
| Colorona Bronze | 62 | | | 38 | | | | 73.4 | 30.6 | 57.8 |
| Colorona Copper | 58 | | | 42 | | | | 65.9 | 38.9 | 42.7 |
| Colorona Copper Fine | 47 | | | 53 | | | | 65.4 | 37.6 | 43.3 |
| Prestige Soft Copper | 31.9 | | | 68.1 | | | | 63.4 | 26.6 | 39 |
| Candurin Orange Amber | 57.5 | | | 42.5 | | | | 66.3 | 39.3 | 43.3 |
| Candurin Brown Amber | 64 | | | 36 | | | | 72.2 | 30.3 | 58 |
| Prestige Bronze | 60.9 | | | 39.1 | | | | 71.5 | 33.2 | 56.6 |
| Prestige Copper | 54.6 | | | 45.4 | | | | 65.7 | 41.1 | 45.6 |
| Sunshine Spectral Copper | | 50 | | 50 | | | | 64.7 | 40.7 | 37.6 |
| Sunshine Spectral Bronze | | 45 | | 55 | | | | 72.3 | 35.9 | 63.3 |
| SynCrystal Soft Peach | | 53 | 17 | 29 | 1 | | | 91.8 | 10.4 | 83.8 |

-continued

| Trade name | Mica | Synthetic fluorphlogopite | TiO2 CI77891 | Iron oxide CI77491 | Tin oxide | Carmin CI75470 | Bismuth oxichloride | L_white | C_white | h_white |
|---|---|---|---|---|---|---|---|---|---|---|
| Red Chromalite | 46 | | | 25 | | | 29 | 55.8 | 45.6 | 36.9 |
| Colorona Bronze Fine | 56 | | | 44 | | | | 72.2 | 29.1 | 54.5 |
| Cloisone Sparkle Bronze | 80 | | | 20 | | | | 86.5 | 18.8 | 62.9 |
| Colorona Sienna Fine | 42 | | | 58 | | | | 64.8 | 37.8 | 33.2 |
| Colorona Russet | 49 | | 1 | 50 | | | | 52 | 34.9 | 31 |
| Prestige Soft Fire | 32.2 | | | 67.8 | | | | 59 | 33.4 | 24.3 |

Even more preferably, the nacres are particles of synthetic fluorphlogopite coated with titanium dioxide, iron oxide and tin oxide, as marketed by Eckart under the name Syncrystal Almond.

The nacres are present in the first laminated coating surrounding the microcapsules core, with a quantity of at least 45% by weight relative to the total weight of a microcapsule, preferably at least 47% by weight, and even better at least 50% by weight. Preferably, their quantity in the first laminated coating surrounding the microcapsules core is less than 70% by weight, preferably less than 65% by weight, even better less than 60% by weight, relative to the total weight of a microcapsule.

The second laminated coating surrounding the first coating of the microcapsules comprises from 10% to 40% by weight of titanium dioxide relative to the total weight of a microcapsule, Preferably, the quantity of titanium dioxide in the second laminated coating of the microcapsules is less than 35% by weight, and better less than 30% by weight relative to the total weight of a microcapsule.

This titanium dioxide may be present as is, or it may be in the form of mica particles coated with titanium dioxide. One example of such particles is the Timica Terra White product MN4501 from BASF.

The second laminated coating surrounding the first coating of the microcapsules can also comprise metal oxides like iron oxides, such as red iron oxides. Preferably, the quantity of metal oxides, preferably iron oxides, in the second laminated coating of the microcapsules is between 1% and 7% by weight, better between 1.5% and 5% by weight relative to the total weight of a microcapsule. Another example of iron oxides is the red iron oxide marketed by Sun under the name Sunpuro Red Iron Oxide C33-8001.

The multilayer interference particles such as nacres according to the invention also include at least one iron oxide, and possibly at least one other metal oxide. Preferably, the microcapsules according to the invention are such that the ratio by weight of (iron oxides):(titanium dioxide), called the ratio X in this application, is between 0.25 and 0.85, preferably between 0.28 and 0.80. The ratio X represents the ratio between the total quantity of iron oxide(s) and the total quantity of titanium dioxide present in the microcapsules. The total quantity of iron oxide(s) corresponds to the iron oxide(s) present in multilayer interference particles, but also to any iron oxides present as such and/or present in other coloring materials of the composition.

Furthermore, the microcapsules according to the invention have a ratio by weight of (multilayer interference particles)/(total pigments), called the ratio Y in this application, equal to at least 0.50, preferably at least 0.60, preferably between 0.50 and 1, and even better between 0.60 and 1. The ratio Y represents the ratio between the total quantity of multilayer interference particles and the total quantity of pigments present in the microcapsules.

The microcapsules can be produced by a known method like that disclosed for example in patent application WO2015/166454. Such methods are also illustrated in example 1.

Composition According to the Invention

Since the composition according to the invention is intended for topical application on the skin or skin appendages, it contains a physiologically acceptable medium. "Physiologically acceptable medium" means a medium compatible with the skin, the lips, the scalp and/or the hair.

The composition according to the invention can be in any galenic form classically used for topical applications and particularly in the form of an aqueous lotion or gel type dispersion, emulsion with liquid to semi-solid consistency obtained by dispersion of a fatty phase in an aqueous phase (O/W) or vice versa (W/O) or an emulsioned cream or gel type liquid to semi-solid suspension. According to one preferred embodiment, the composition is in the form of a direct emulsion (O/W) or the inverse (W/O) or in gel form.

It can also be used as a foundation to be applied to the face or the neck, an under-eye concealer, or a skin care cream.

According to one particular embodiment, the composition according to this invention has a low content of additional coloring materials, different from the coloring materials present in the microcapsules and described above.

According to one even more particular embodiment, the composition according to this invention has no additional coloring materials.

A composition with "no additional coloring materials" means that a composition according to the invention may comprise a very low content of coloring materials, namely less than 0.1% by weight, or even less than 0.01% by weight, preferably less than 0.001% by weight, even better less than 0.0005% by weight relative to the total weight of the composition.

According to one variant of the invention, a composition according to the invention comprises at least one aqueous phase, and particularly water.

This aqueous phase may be composed wholly or partly of water, and is preferably composed essentially of water.

A composition according to the invention can thus comprise a water content of between 1% and 90% by weight of water, preferably more than 50% by weight of water or even more than 60% by weight of water, preferably more than 70% by weight of water relative to the total weight of the composition.

According to one preferred embodiment, a composition according to the invention comprises between 50% and 90% by weight of water, preferably between 60% and 90% by weight of water, and even better between 70% and 80% by weight of water relative to the total weight of the composition.

The aqueous phase of a composition according to the invention may also be composed of a mix of water and an organic solvent miscible with water such as lower monoalcohols with between 2 and 5 carbon atoms such as ethanol, isopropanol, glycols with 2 to 8 carbon atoms such as propylene glycol, glycerol, ethylene glycol, 1,3-butylene glycol, dipropylene glycol, ketones in $C_3$-$C_4$, and aldehydes in $C_2$-$C_4$, preferably a glycol with 2 to 8 carbon atom, preferably glycerol.

A composition according to the invention may also have a fatty phase, preferably a fatty phase dispersed in the continuous aqueous phase disclosed above, so as to form an oil-in-water, water-in oil type emulsion, and preferably oil-in-water.

An emulsion according to the invention may also be in the form of a multiple emulsion, namely of the water-in-oil-in-water or oil-in-water-in-oil type.

The fatty phase of a composition according to the invention may in particular comprise at least one fatty body that is liquid at ambient temperature and/or a fatty body that is solid at ambient temperature, such as waxes, pasty fatty bodies, gums and mixtures thereof.

For the purposes of the invention, the term "ambient temperature" means a temperature equal to 25° C.

The fatty phase of the composition according to the invention may comprise particularly at least one volatile or non-volatile oil or mixtures thereof, as the liquid fatty body.

The term "volatile oil" for the purposes of the invention denotes any oil capable of evaporating on contact with skin in less than one hour, at ambient temperature and at atmospheric pressure.

The term "non-volatile oil" denotes an oil remaining on skin at ambient temperature and atmospheric pressure for at least several hours and particularly having a vapor pressure less than 0.01 mm Hg (1.33 Pa).

These volatile or non-volatile oils may be hydrocarbon oils, silicone oils or mixtures thereof. A "hydrocarbon oil" is an oil containing principally hydrogen and carbon atoms and possible oxygen, nitrogen, sulfur and phosphorus atoms.

Volatile hydrocarbon oils can be chosen from among hydrocarbon oils having 8 to 16 carbon atoms, and particularly branched alkanes in $C_8$-$C_{16}$ such as petroleum-based isoalkanes in $C_8$-$C_{16}$ (also referred to as isoparaffins) such as isododecane (also referred to as 2,2,4,4,6-pentamethylheptane), isodecane, isohexadecane, and for example oils sold under the trade names Isopars® or Permetyls®, branched esters in $C_8$-$C_{16}$ such as iso-hexyl neopentanoate, and mixtures thereof. Further volatile hydrocarbon oils such as petroleum distillates, particularly those sold under the name Shell Solt® by SHELL, may also be used.

Other volatile oils that can be used are volatile silicones, such as for example volatile linear or cyclic silicone oils, particularly those having a viscosity ≤ of 8 centistokes ($8 \times 10^{-6}$ m$^2$/s), and in particular having 2 to 7 silicon atoms, these silicones optionally comprising alkyl or alkoxy groups having 1 to 10 carbon atoms. Mention may be made, as a volatile silicone oil suitable for use in the invention, in particular, of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane, dodecamethyl pentasiloxane, and mixtures thereof.

The volatile oil can be present in a composition according to the invention with a content ranging from 0.1% to 98% by weight, preferably from 1% to 65% by weight and in particular from 2% to 50% by weight in relation to the total weight of the composition.

The non-volatile oils may, in particular, be chosen from among non-volatile, fluorinated and/or silicone hydrocarbon oils.

As a non-volatile hydrocarbon oil, mention may be made of:
hydrocarbon oils of animal origin,
hydrocarbon oils of plant origin such as triglycerides constituted of fatty acid esters and glycerol for which the fatty acids can have chain lengths ranging from $C_4$ to $C_{24}$, with the latter able to be linear or branched, saturated or unsaturated; these oils are in particular wheat germ, sunflower, grape seed, sesame, corn, apricot, castor, shea, avocado, olive, soybean oils, sweet almond, palm, cotton, hazelnut, macadamia, jojoba, alfalfa, poppy seed, pumpkin, sesame, squash, rapeseed, blackcurrant, evening primrose, millet, barley, quinoa, rye, safflower, candlenut, passiflora, musk rose oil; or caprylic/capric acid triglycerides such as those sold by Stearineries Dubois or those sold under the trade names Miglyol 810, 812 and 818® by Dynamit Nobel,
synthetic ethers having from 10 to 40 carbon atoms;
linear or branched hydrocarbons of mineral or synthetic origin, such as petroleum jelly, polydecenes, hydrogenated polyisobutene such as Parleam, squalane, and mixtures thereof, preferably petroleum jelly;
synthetic esters such as oils having the formula $R_1COOR_2$ in which $R_1$ represents the residue of a linear or branched fatty acid comprising 1 to 40 carbon atoms and $R_2$ represents a hydrocarbon chain, particularly branched containing 1 to 40 carbon atoms on the condition that $R_1+R_2$ is ≥10, such as for example Purcellin oil (cetostearyl octanoate), isopropyl myristate, isopropyl palmitate, $C_{12}$ to $C_{15}$ alcohol benzoates, hexyl laurate, diisopropyl adipate, isononyl isononanoate, 2-ethylhexyl palmitate, isostearyl isostearate, heptanoates, octanoates decanoates or ricinoleates of alcohols or polyalcohols such as propylene glycol dioctanoate; hydroxylated esters, such as isostearyl lactate, diisostearyl malate; polyol esters and pentaerythritol esters,
fatty alcohols that are liquid at ambient temperature, with a branched and/or unsaturated carbon chain having 12 to 26 carbon atoms, such as octyldodecanol, isostearyl alcohol, oleic alcohol, 2-hexyldecanol, 2-butyloctanol, 2-undecylpentadecanol and;
higher fatty acids, such as oleic acid, linoleic acid, linolenic acid, and mixtures thereof.

The non-volatile silicone oils that can be used in the composition in accordance with the invention can be non-volatile polydimethylsiloxanes (PDMS), polydimethylsiloxanes comprising alkyl or alkoxy groups which are pendant or at the end of the silicone chain, groups each having 2 to 24 carbon atoms; phenylated silicones, such as phenyl trimethicones, phenyl dimethicones, phenyltrimethylsiloxy-diphenylsiloxanes, diphenyl dimethicones, diphenylmethyl-diphenyl-trisiloxanes or (2-phenylethyl)trimethylsiloxysilicates.

Non-volatile oils can be present in a composition according to the invention with a content ranging from 0.01% to 90% by weight, preferably from 0.1% to 85% by weight and in particular from 1% to 70% by weight in relation to the total weight of the composition.

A composition according to the invention may also contain surfactants present particularly in a proportion ranging from 0.1% to 30% by weight, and preferably from 1% to 15% by weight, relative to the total weight of the composition.

These surfactants may be chosen from among anionic, cationic, amphoteric or non-ionic surfactants. Reference may be made to the document "Encyclopedia of Chemical Technology, KIRK-OTHMER", volume 22, pp 333-432, 3rd edition, 1979, WILEY, for the definition of the properties and emulsifying functions of surfactants, in particular pp 347-377 of this reference, for anionic and non-ionic surfactants.

A composition according to the invention may further contain at least one gelling agent and/or thickener. The gelling agent and/or thickener can be present in the composition according to the invention in a content ranging from 0.01% to 10% by weight, particular from 0.1% to 1% by weight in relation to the total weight of the composition.

The thickeners according to the invention can be of natural or synthetic, mineral or organic origin.

The thickeners can be anionic, cationic, amphoteric or non-ionic polymers, associative or not.

Preferred thickeners and/or gelling agents are hydrophilic thickeners and/or gelling agents, in other words soluble or dispersible in water. By way of hydrophilic gelling agents, mention may be made for example of optionally modified carboxyvinyl polymers, such as the products marketed under the trade names Carbopol (CTFA name: carbomer) and Pemulen (CTFA name: Acrylates/C 10-30 alkyl acrylate crosspolymer) by Goodrich; polyacrylamides; 2-acrylamido 2-methylpropane sulfonic acid polymers and copolymers (AMPS), optionally cross-linked and/or neutralized, such as poly(2-acrylamido-2-methylpropanesulfonic acid) marketed by Hoechst under the trade name "Hostacerin AMPS" (CTFA name: Ammonium Polyacryldimethyltauramide); cross-linked anionic acrylamide/AMPS copolymers, in the form of a W/O emulsion, such as those marketed under the name SEPIGEL 305 (C.T.F.A. name: Polyacrylamide/C13-14 Isoparaffin/Laureth-7) and under the name SIMULGEL 600 (C.T.F.A. name: Acrylamide/Sodium acryloyldimethyltaurate copolymer/Isohexadecane/Polysorbate 80) by SEPIC; polysaccharide biopolymers such as xanthan gum, guar gum, alginates, modified celluloses; and mixtures thereof.

The mineral thickeners can be chosen from clays, optionally modified, silicas, optionally modified, or mixtures thereof.

Preferably, the mineral thickeners are chosen from lipophilic clays in particular modified hectorites; pyrogenic silica with a hydrophobic treatment; hydrophobic silica aerogels, or mixtures thereof.

The composition according to this invention can furthermore contain various adjuvants that are commonly used in the cosmetics field, such as fillers; preservatives; sequestering agents; perfumes; pH agents.

The following examples illustrate the invention without being in any way limitative. Unless mentioned otherwise, the quantities indicated are expressed as a percentage by mass.

EXAMPLES

Example 1: Preparations of Microcapsules

I. Microcapsules

Different examples of the preparation of microcapsules according to the invention are described below to illustrate the invention.

The following particles are used in the examples:
red iron oxide particles (Sunpuro Red Iron Oxide C33-8001),
titanium dioxide particles (HOMBITAN FF-PHARMA),
different fluorphlogopite particles coated with a mix of titanium dioxide, tin oxide and iron oxide (Syncrystal® Almond from Eckart), and
mica particles coated with titanium dioxide (Timica® Terra White MN4501 from BASF).

Examples 1a to 1f

Microcapsules according to the invention (1a, 1 b and 1e) and comparative microcapsules (1c, 1d, 1f and 1g) are prepared using the following method:
a) preparation of an aqueous solution containing water, starch and a polyvinyl alcohol (binder),
b) the dispersion of multilayer interference particles (i.e. in this case Syncrystal® Almond or Timica® Terra White MN4501 for comparative microcapsules 1c) in the aqueous solution obtained in a),
c) formation of an internal layer (i.e. the first laminated coating) on the mannitol core with the aqueous solution obtained in b),
d) formation of an intermediate layer (i.e. the second laminated coating) on the internal layer obtained in c) with a solution of titanium dioxide (HOMBITAN FF-PHARMA or present in Timica® Terra White MN4501 nacres for microcapsules according to the invention 1e) containing water, starch, hydrogenated lecithin and possibly red iron oxides and polyvinyl alcohol, and
e) formation of an external layer on the intermediate layer obtained in d) with an aqueous starch solution possibly containing hydrogenated lecithin.

The following microcapsules are thus obtained:

| | | | 1b According to the invention White to red | 1f White to red | 1d White to red | 1g White to red | 1c White | 1a According to the invention Pink to red | 1e According to the invention Pink to red |
|---|---|---|---|---|---|---|---|---|---|
| Composition | Intermediate layer (second laminated coating) | Red iron oxide | — | — | — | — | — | 3 | 3 |
| | | Titanium dioxide (HOMBITAN FF-PHARMA) | 28 | 55 | 65 | 25 | 28 | 25 | — |

-continued

| Description | | | 1b According to the invention White to red | 1f White to red | 1d White to red | 1g White to red | 1c White | 1a According to the invention Pink to red | 1e According to the invention Pink to red |
|---|---|---|---|---|---|---|---|---|---|
| | Internal layer (first laminated coating) | White nacre (Timica® Terra White MN4501) | — | — | — | 40 | — | — | 25 |
| | | Red nacre (Syncrystal® Almond) | 51 | 23 | 18 | 20 | — | 52 | 52 |
| | | White nacre (Timica® Terra White MN4501) | — | — | — | — | 51 | — | — |
| | Core | Mannitol | 15 | 18 | 14 | 8 | 15 | 15 | 15 |
| | Binder | — | QSP | QSP | QSP | QSP | QSP | QSP | QSP |
| Ratio X* | | | — | 0.30 | 0.08 | 0.05 | 0.09 | 0.00 | 0.43 | 0.76 |
| Ratio Y* | | | — | 0.65 | 0.29 | 0.22 | 0.70 | 0.65 | 0.65 | 0.96 |

*as indicated in the description above

The microcapsules according to comparative examples 1f and 1g above are prepared as described in the above methods.

Example 2: Preparation of Microcapsules Containing Syncrystal® Almond Using a Fluidized Bed Method The coating of the internal layer is applied using a bottom spray system. Firstly, the Pearlitol 100SD basic material (mannitol) is added to the system (step No. 1). The 1st coating solution contains Syncrystal® Almond, Structure XL (starch) and PVA S205 (polyvinyl alcohol) particles (steps No. 2-3). Firstly, a 5% solution of PVA S205 was prepared from 0.83% of solid PVA S205 by adding 5% by weight of 0.83% of solid PVA to 95% of stirred hot water. For better dispersion, Syncrystal® Almond and Structure XL particles were added to the water purified above and homogenized. The 5% solution of PVA prepared above was added to the homogenized solution and thoroughly mixed. The solution of the first prepared laminated coating was loaded into the machine before being sprayed on floating Pearlitol 100SD through the nozzle fixed to the bottom of the machine. The second laminated coating was also made using a bottom spray system. The capsules with the color of the internal core coated with 52.05% of Syncrystal® Almond particles by the first coating were sorted and selected before being loaded into the machine at a ratio of 70% weight/weight of the final composition. The solution of the second laminated coating contains HOMBITAN FF-PHARMA, red iron oxide, Structure XL, PVA S205 and Lipoid P 75-3 (steps 5-9). Firstly, a 5% solution of PVA S205 is prepared from 0.26% of solid PVA S205 by adding a 5% quantity of 0.26% of solid PVA to 95% of stirred hot water. The remainder of the solution of the second laminated coating is prepared carefully mixing 200% by weight/weight of purified water, of HOMBITAN FF-PHARMA, red iron oxide, Structure XL (steps No. 5, 6, 7) and Lipoid P 75-3 (step No. 9). Dispersion is made more uniform by adding 10% by weight/weight of the solution of the second laminated coating of ethanol and it is well mixed using a homogenizer. The solution of the second laminated coating was loaded into the machine and sprayed on 70% of the colored internal core through the nozzle located at the bottom of the machine.

The coating of the third layer (external layer) was applied immediately after the second laminated coating was coated without filtering or sorting. The binder (corn starch) (step No. 10) was prepared by mixing 0.1% by weight/weight of the entire composition of corn starch dispersed in purified water (1:1), then mixed with 20% by weight/weight of the total weight of the composition of purified hot water at 95° C. The external layer is intended to clear cloudiness in the final product and it is sprayed until after the end of the second coating.

The coated particles finally obtained are pink pearls containing a magic capsule expressing an instantaneous pink pearly effect. The size of the particles is 75 to 300 μm with the following composition:

| Method | Detail | Step | Raw material | Composition | INCI name |
|---|---|---|---|---|---|
| Colored internal core | Core | 1 | Pearlitol 100SD | 15.05% | Mannitol |
| | First laminated coating | 2 | Syncrystal Almond | 52.05% | Titanium dioxide/ diiron trioxide/tin dioxide/ synthetic fluorphlogopite |
| | | 3 | Structure XL | 2.49% | Hydroxypropyl Starch Phosphate |

-continued

| Method | Detail | Step | Raw material | Composition | INCI name |
|---|---|---|---|---|---|
| Colored external coating | Second laminated coating | 4 | PVA S205 | 0.83% | Polyvinyl alcohol |
| | | 5 | HOMBITAN FF-PHARMA | 25.20% | Titanium dioxide, |
| | | 6 | Red Iron Oxide | 2.80% | Iron Oxides (CI 77491) |
| | | 7 | Structure XL | 1.05% | Hydroxypropyl Starch Phosphate |
| | | 8 | PVA S205 | 0.26% | Polyvinyl alcohol |
| | | 9 | Lipoid P 75-3 | 0.17% | Hydrogenated Lecithin |
| | External layer | 10 | Corn Starch Binder | 0.10% | *Zea Mays*(corn) Starch |
| | Total | | | 100.00% | |

Example 3: Healthy-Looking Appearance Composition in the Form of an O/W Emulsion Compositions A to F below were prepared using techniques known to an expert in the subject.

| | | COMPOSITIONS | | | | | |
|---|---|---|---|---|---|---|---|
| | | A | B | C | D | E | F |
| | | According to the invention | | | comparative | | |
| Phase | INGREDIENTS | | | | | | |
| Aqueous phase | WATER | QSP 100 | QSP 100 | QSP 100 | QSP 100 | QSP 100 | QSP 100 |
| | GLYCERIN | 8.5 | 8.5 | 8.5 | 8.5 | 8.5 | 8.5 |
| | PRESERVATIVE | QS | QS | QS | QS | QS | QS |
| | TETRASODIUM EDTA | 0.10 | 0.10 | 0.10 | 0.10 | 0.10 | 0.10 |
| | ACRYLAMIDE/SODIUM ACRYLOYLDIMETHYL-TAURATE COPOLYMER (and) ISOHEXADECANE (and) POLYSORBATE 80 (SIMULGEL 600 sold by SEPPIC) | 1.5 | 1.5 | 1.5 | 1.5 | 1.5 | 1.5 |
| Oily phase | SORBITAN TRISTEARATE | 1 | 1 | 1 | 1 | 1 | 1 |
| | PEG-40 DISTEARATE [(4)] | 2 | 2 | 2 | 2 | 2 | 2 |
| | CETYL ALCOHOL | 3.5 | 3.5 | 3.5 | 3.5 | 3.5 | 3.5 |
| | GLYCEROL STEARATE | 2.8 | 2.8 | 2.8 | 2.8 | 2.8 | 2.8 |
| | ISOSTEARYL NEOPENTANOATE | 5 | 5 | 5 | 5 | 5 | 5 |
| | HYDROGENATED POLYISOBUTENE | 5 | 5 | 5 | 5 | 5 | 5 |
| | MINERAL OIL | 4 | 4 | 4 | 4 | 4 | 4 |
| | DIMETHICONE | 8 | 8 | 8 | 8 | 8 | 8 |
| | Microcapsules in example 1a | 2 | — | | | | |
| | Microcapsules in example 1b | | 2 | — | | | |
| | Syncrystal ® Almond (Eckart) | | | — | 1 | | |
| | Microcapsules in example 1c | | | — | | 2 | |
| | Microcapsules in example 1d | | | — | | | 2 |

For each composition A to F, cosmetic properties were evaluated using the following protocol. The cosmetic properties in application are evaluated in a monadic approach by a panel of experts trained in the description of care products. The sensorial evaluation of care products by this panel is made as follows: products are conditioned in opaque pots or pump bottles depending on the viscosity of the products. Samples within a particular session are presented in random order for each panelist.

Comparative Evaluation of Cosmeticity/Sensorial Properties

The 15 experts evaluated the following sensorial properties:

The "slip" of the composition during application (that opposes the retarding effect of compositions that stick during application)

The softness of the skin finish once the composition has been applied (that opposes the rough, brittle effect)

Comfort. A comfortable product is defined as a product that does not pull, that does not dry the skin and that transports a care effect Moisturization, esthetic expert evaluation on face and eye dehydration lines.

Descriptors are evaluated on a scale of 5 levels: ++/+/0/−/−−

Evaluation of the Healthy-Looking Appearance

Immediate esthetic evaluation of the composition according to the invention:

Healthy glow: emphasize the color and/or add light and radiance, with becoming shiny.

Natural effect: the match between the skin finish of the product and the color of the consumer's skin Covering effect: lack of homogeneity in application, problem of traces and lack of homogeneity after application Descriptors are evaluated on a scale of 5 levels: ++/+/0/−/−−

On the different phenotypes: white color (phototype I), on intermediate color (phototype III) to mat color (phototype IV/V).

The results are collected below:

|  |  | COMPO A (invention) | COMPO B (invention) | COMPO C | COMPO D | COMPO E | COMPO F |
|---|---|---|---|---|---|---|---|
| Sensorial Aspects | Slip during application | ++ | ++ | ++ | − | ++ | ++ |
|  | Softness of the skin finish | ++ | ++ | ++ | − | ++ | ++ |
|  | Comfort | ++ | ++ | ++ | −− | ++ | ++ |
|  | Sensorial properties | OK | OK | OK | Not OK | OK | OK |
| Immediate esthetic evaluation on intermediate color (phototype III) | Evaluation of the healthy-looking appearance | ++ | ++ | −− | + | −− | 0 |
|  | Natural effect | ++ | ++ | −− | + | − | + |
|  | Covering effect | −− | −− | −− | + | − | −− |
|  | healthy-looking appearance | OK | OK | Not OK | OK | Not OK | Not OK |

Conclusion:

In general, the introduction of microcapsules according to the invention does not have any negative impact on the cosmeticity of the base.

Compositions A and B according to the invention have the special feature that:

They do not have a covering effect (homogeneity in application),

They provide a very natural skin effect, regardless of the complexion/phototype of the skin on which the composition is applied, They do not introduce any negative effect on cosmeticity of the composition.

Example 4: Healthy-Looking Appearance Composition in the Form of a Gel

| INCI name | COMPOSITION G (comparative) | COMPOSITION H (invention) |
|---|---|---|
| Water | QSP | QSP |
| GLYCERIN | 9 | 9 |
| PRESERVATIVE | QS | QS |
| PEG-20 | 1 | 1 |
| PROPYLENE GLYCOL | 2 | 2 |
| BUTYLENE GLYCOL | 2 | 2 |
| PEG-8 | 1.1 | 1.1 |
| BIS-PEG-18 METHYL ETHER DIMETHYL SILANE | 0.5 | 0.5 |
| CARBOMER | 0.3 | 0.3 |
| POTASSIUM HYDROXIDE | 0.09 | 0.09 |
| PEG-40 HYDROGENATED CASTOR OIL | 0.30 | 0.30 |
| Ethanol | 3 | 3 |
| Microcapsules according to example 1a | / | 2 |

Procedure: Compositions G and H are classical gels for which the manufacturing method is known to an expert in the subject.

The cosmeticity/sensorial properties of compositions G and H above are evaluated as described in example 3.

In general, the introduction of microcapsules according to example 1a does not have any negative impact on the cosmeticity of the base. Compositions G and H are sensorially very similar. Composition H according to the invention during application has the same slip as formula G, and the skin finish is equally soft. No difference is found during the expert evaluation of the moisturizing effect of these two formulas: composition H according to the invention has good moisturizing properties (face and eye contour).

Evaluation of the Healthy-Looking Appearance of Formula H According to the Invention

|  | Evaluation of the healthy-looking appearance | Natural effect | Covering effect |
|---|---|---|---|
| On white color (phenotype etc.) | ++ Enhanced skin color + added radiance | ++ | – – Good homogeneity in application |
| On intermediate color (phenotype etc.) | ++ Enhanced skin color + added radiance | ++ | – – Good homogeneity in application |
| On matte color (phenotype etc.) | ++ provides radiance, light, without shiny effect | ++ | – – Good homogeneity in application |

In summary: composition H according to the invention is specific in that:
- it does not have a covering effect (homogeneity in application),
- it provides a very natural effect, regardless of the complexion/phenotype of the skin on which the product is applied,
- it has no negative effect on the cosmeticity of the base.

Furthermore, composition H has an esthetic benefit due to the presence of colored balls.

Example 5: Healthy-Looking Appearance Composition in the Form of an O/W Emulsion

| Phase | INGREDIENTS | Composition I OUTSIDE INVENTION | Composition J ACCORDING TO THE INVENTION |
|---|---|---|---|
| Aqueous phase | WATER | QSP 100 | QSP 100 |
|  | GLYCERIN | 9 | 9 |
|  | PRESERVATIVE | QS | QS |
|  | DISODIUM EDTA | 0.1 | 0.1 |
|  | AMMONIUM POLYACRYLOYLDIMETHYL TAURATE (HOSTACERIN AMPS sold by CLARIANT) | 1 | 1 |
| Aqueous phase | POLYACRYLAMIDE (and) C13-14 ISOPARAFFIN (and) LAURETH-7 (SEPIGEL 305 sold by SEPPIC) | 0.9 | 0.9 |
| Oily phase | CETYL ALCOHOL | 1.5 | 1.5 |
|  | PEG-100 STEARATE (MYRJ S100-PA-(SG) sold by CRODA) | 0.20 | 0.20 |
|  | ISOHEXADECANE | 3 | 3 |
|  | DISODIUM STEAROYL GLUTAMATE | 0.30 | 0.30 |
|  | CETEARYLIC ALCOHOL (and) CETEARYL GLUCOSIDE | 0.60 | 0.60 |
|  | STEARIC ACID | 0.6 | 0.6 |
|  | BEHENYLIC ALCOHOL | 1.65 | 1.65 |
|  | SQUALANE | 1 | 1 |
|  | MINERAL OIL | 1 | 1 |
|  | ISOSTEARYL NEOPENTANOATE | 4.5 | 4.5 |
|  | DIMETHICONE | 2 | 2 |
|  | Microcapsules according to example 1a | / | 2 |

The compositions were prepared using techniques known to an expert in the subject. Cosmetic properties were evaluated for each of the compositions I and J using the protocol described in example 3 above.

The results are collected below.

In general, the introduction of microcapsules according to the invention does not have any negative impact on the cosmeticity of the base, and cosmeticity/sensorial properties. Compositions I and J are sensorially very similar. Composition J according to the invention has the same slip during application as composition I that is not according to the invention, and the skin finish is equally soft. No difference is found during the expert evaluation of the moisturizing effect of these 2 formulas: composition J according to the invention has good moisturizing properties (face and eye contour).

Evaluation of the Healthy-Looking Appearance of Composition J According to the Invention The healthy-looking appearance was evaluated according to the protocol presented above in example 3.

The results are collected in the following table.

|  | Evaluation of the healthy-looking appearance | Natural effect | Covering effect |
| --- | --- | --- | --- |
| On white color (phenotype etc.) | ++ Enhanced skin color + provides radiance | ++ | – – Good homogeneity in application |
| On intermediate color (phenotype etc.) | ++ Enhanced skin color + provides radiance | ++ | – – Good homogeneity in application |
| On matte color (phenotype etc.) | ++ provides radiance, light, without shiny effect | ++ | – – Good homogeneity in application |

In summary: composition J according to the invention is specific in that:
- It does not have a covering effect (homogeneity in application),
- It provides a very natural skin effect, regardless of the complexion/phototype of the skin on which the composition is applied,
- It does not introduce any negative impact on cosmeticity of the composition.

Example 6: Composition of the Healthy-Looking Appearance in the Form of an Inverse (W/O) Emulsion

| Phase | INGREDIENTS | Composition K OUTSIDE INVENTION | Composition L ACCORDING TO THE INVENTION |
| --- | --- | --- | --- |
| Aqueous phase | WATER | QSP 100 | QSP 100 |
|  | GLYCERIN | 9 | 9 |
|  | PRESERVATIVE | QS | QS |
|  | SODIUM POLYACRYLATE | 0.45 | 0.45 |
|  | DISODIUM EDTA | 0.1 | 0.1 |
|  | SODIUM ACRYLATESCOPOLYMER (and) CAPRYLIC/CAPRIC TRIGLYCERIDE (LUVIGEL EM sold by BASF) | 2.00 | 2.00 |
| Oily phase | DIMETHICONE (and) DIMETHICONE/PEG-10/15 CROSSPOLYMER (KSG-210 sold by SHIN ETSU) | 4.5 | 4.5 |
|  | DIMETHICONE(and) DIMETHICONE/POLYGLYCERIN-3 CROSSPOLYMER (KSG-710 sold by SHIN ETSU) | 4 | 4 |
|  | ISOHEXADECANE | 4 | 4 |
|  | CYCLOHEXASILOXANE | 2 | 2 |
|  | DIMETHICONE | 5 | 5 |
|  | PEG-10 DIMETHICONE | 1 | 1 |
|  | DISTEARDIMONIUM HECTORITE | 0.65 | 0.65 |
| Denatured alcohol | DENATURED ALCOHOL | 1.5 | 1.5 |
|  | Microcapsules according to example 1b | / | 2 |

The compositions were prepared using techniques known to an expert in the subject.

Cosmetic properties were evaluated for each of the compositions K and L using the protocol described in example 3 above.

The results are collected below.

In general, the introduction of microcapsules according to the invention does not have any negative impact on the cosmeticity of the base and cosmeticity/sensorial properties.

Compositions K and L are sensorially very similar. Composition L according to the invention has the same slip during application as formula K, and the skin finish is equally soft. No difference is found during the expert evaluation of the moisturizing effect of these 2 formulas: composition L according to the invention has good moisturizing properties (face and eye contour).

Evaluation of the Healthy-Looking Appearance of Formula L According to the Invention

|  | Evaluation of the healthy-looking appearance | Natural effect | Covering effect |
| --- | --- | --- | --- |
| On white color (phenotype etc.) | ++ Enhanced skin color + provides radiance | ++ | – – Good homogeneity in application |
| On intermediate color (phenotype etc.) | ++ Enhanced skin color + provides radiance | ++ | – – Good homogeneity in application |
| On matte color (phenotype etc.) | ++ provides radiance, light, without shiny effect | ++ | – – Good homogeneity in application |

In summary: the composition according to the invention is specific in that:

It does not have a covering effect (homogeneity in application),

It provides a very natural skin effect, regardless of the complexion/phototype of the skin on which the composition is applied, It does not introduce any negative effect on the cosmeticity of the composition.

Example 7: Comparison Between a Composition According to the Invention and a Composition Comprising the Same Dyes but without a Microcapsule A formula according to the invention (M) is compared with a formula containing the same coloring materials in the same quantities, but without a microcapsule (formula N).

The following compositions are prepared using techniques known to an expert in the subject.

| Phase | INCI name | Composition M | Composition N (comparative) |
| --- | --- | --- | --- |
| Aqueous phase | WATER | QSP | QSP |
|  | GLYCERIN | 8.5 | 8.5 |
|  | PRESERVATIVE | QS | QS |
|  | TETRASODIUM EDTA | 0.10 | 0.10 |
|  | ACRYLAMIDE/SODIUM ACRYLOYLDIMETHYLTAURATE COPOLYMER (and) ISOHEXADECANE (and) POLYSORBATE 80 | 1.5 | 1.5 |
| Oily phase | SORBITAN TRISTEARATE | 1 | 1 |
|  | PEG-40 DISTEARATE (4) | 2 | 2 |
|  | CETYL ALCOHOL | 3.5 | 3.5 |
|  | GLYCEROL STEARATE | 2.8 | 2.8 |
|  | ISOSTEARYL NEOPENTANOATE | 5 | 5 |
|  | HYDROGENATED POLYISOBUTENE | 5 | 5 |
|  | MINERAL OIL | 4 | 4 |
|  | DIMETHICONE | 8 | 8 |
|  | Microcapsules according to example 1a | 3 |  |
|  | Red iron oxide (Sunpuro Red Iron Oxide C33-8001) |  | 3%*0.03 = 0.09% |
|  | Titanium dioxide (HOMBITAN FF-PHARMA), |  | 25%*0.03 = 0.75% |
|  | Red nacre (Syncrystal ® Almond from Eckart) |  | 52%*0.03 = 1.56% |

Cosmetic properties were evaluated for each of the compositions M and N using the protocol described in example 3 above.

The results are collected below.

Comparative Evaluation of the Different Formulas

|  |  | Composition M ACCORDING TO THE INVENTION | Composition N OUTSIDE INVENTION |
|---|---|---|---|
| Sensorial Aspects | Slip during application | ++ | – – |
|  | Softness of the skin finish | ++ | – – |
|  | Comfort | ++ | – – |
| Immediate esthetic evaluation on intermediate color (phototype III) | Evaluation of the healthy-looking appearance | ++ | + + |
|  | Natural effect | ++ | – |
|  | Covering effect | – – | 0 |

In summary: composition N slips less, is not as soft as and is less comfortable than composition M.

Composition M according to the invention is specific in that:
- it does not have a covering effect (homogeneity in application),
- it has a very natural skin effect (in this case on phenotype 3),
- good cosmeticity of the product during application and after application (no drying effect, astringent agent that does not transport equally good moisturization).

Composition N can induce non-homogeneities during application, making the skin finish only slightly homogeneous and not very natural.

The invention claimed is:

1. A cosmetic composition comprising, in a physiologically acceptable medium, at least one microcapsule comprising at least:
   a core,
   a first laminated coating surrounding said core comprising at least 45% by weight of the total weight, of a microcapsule of multilayer interference particles comprising at least one iron oxide, and
   a second laminated coating surrounding said first coating, comprising between 10% and 40% by weight of titanium dioxide relative to the total weight of a microcapsule,
   said multilayer interference particles being released from said at least one microcapsule only when said composition is applied on a keratin material,
   wherein the ratio by weight between the total quantity of the at least one iron oxide and the total quantity of titanium dioxide present in the microcapsules is between 0.25 and 0.85 and wherein the ratio by weight between the total quantity of multilayer interference particles and the total quantity of pigments present in the microcapsules is equal to at least 0.50,
   wherein the composition contains at least one fatty phase and/or at least one surfactant.

2. The cosmetic composition according to claim 1, in which the multilayer interference particles comprising at least one iron oxide are nacres.

3. The cosmetic composition according to claim 2, comprising between 0.1% and 20% by weight of microcapsules relative to the total weight of said composition.

4. The cosmetic composition according to claim 2, in which the core is organic and comprises at least one monosaccharide or its derivatives.

5. The cosmetic composition according to claim 1, comprising between 0.1% and 20% by weight of microcapsules relative to the total weight of said composition.

6. The cosmetic composition according to claim 2, comprising between 0.1% and 5% by weight of multilayer interference particles comprising at least one iron oxide relative to the total weight of said composition.

7. The cosmetic composition according to claim 5, in which the core is organic and comprises at least one monosaccharide or its derivatives.

8. The cosmetic composition according to claim 5, comprising between 0.1% and 5% by weight of multilayer interference particles comprising at least one iron oxide relative to the total weight of said composition.

9. The cosmetic composition according to claim 1, in which the core is organic and comprises at least one monosaccharide or its derivatives.

10. The cosmetic composition according to claim 9, comprising between 0.1% and 5% by weight of multilayer interference particles comprising at least one iron oxide relative to the total weight of said composition.

11. The cosmetic composition according to claim 1, comprising between 0.1% and 5% by weight of multilayer interference particles comprising at least one iron oxide relative to the total weight of said composition.

12. The cosmetic composition according to claim 1, in which the multilayer interference particles comprising at least one iron oxide are nacres present in the first laminated coating, in an amount of at least 47% by weight relative to the total weight of a microcapsule.

13. The cosmetic composition according to claim 1, in which the quantity of titanium dioxide in the second laminated coating is less than 35% by weight relative to the total weight of a microcapsule.

14. The cosmetic composition according to claim 1, in which the second laminated coating comprises metal oxides.

15. The cosmetic composition according to claim 14, in which the quantity of metal oxides present is between 1% and 7% by weight relative to the total weight of a microcapsule.

16. The cosmetic composition according to claim 1, in which the multilayer interference particles comprising at least one iron oxide comprise at least one other metal oxide.

17. The cosmetic composition according to claim 1, in which the ratio by weight between the total quantity of the at least one iron oxide and the total quantity of titanium dioxide present in the microcapsules is between 0.28 and 0.80.

18. The cosmetic composition according to claim 1, in which the ratio by weight between the total quantity of multilayer interference particles and the total quantity of pigments present in the microcapsules is equal to at least 0.60.

19. The cosmetic composition according to claim 1, in which said composition is in the form of an aqueous lotion or gel type dispersion, emulsion with liquid to semi-solid consistency obtained by dispersion of a fatty phase in an aqueous phase (O/W) or vice versa (W/O) or an emulsified cream or gel type liquid to semi-solid suspension.

20. A method of conferring a homogeneous appearance and a pinkish tone on skin, while preserving the natural appearance of the skin, comprising applying at least one layer of a composition as defined in claim 1 on the surface of the target skin.

* * * * *